United States Patent [19]
Calange et al.

[11] Patent Number: 6,042,715
[45] Date of Patent: Mar. 28, 2000

[54] METHOD FOR MODELING THE CRYSTALLIZATION OF PARAFFINS IN PETROLEUM FLUIDS

[75] Inventors: Sandra Calange, St-Germain-en-Laye; Véronique Ruffier-Meray, Poissy; Emmanuel Behar, Jouiy le Moutier, all of France

[73] Assignee: Institut Francais du Petrole, Rueil-Malmaison, France

[21] Appl. No.: 08/931,656

[22] Filed: Sep. 16, 1997

[51] Int. Cl.⁷ .................................................... C10B 73/00
[52] U.S. Cl. ................................ 208/24; 208/27; 208/37; 208/309; 208/351; 585/501; 436/55
[58] Field of Search .................................. 208/37, 24, 27, 208/309; 585/501; 436/55

[56] References Cited

PUBLICATIONS

SPE International Symposium on Oilfield Chemistry, 18–2 Fevrier 1997, Texas USA pp. 283–290, Calange et al "Onset Crystallization Temperature and Deposit Amount for Waxy Crudes: Experimental Determination and Thermodynamic Modelling."

*Primary Examiner*—Helane Myers
*Attorney, Agent, or Firm*—Antonelli, Terry, Stout & Kraus, LLP

[57] ABSTRACT

A thermodynamic model is formed which allows determination of the temperature at which waxes or paraffins appear in petroleum fluids, and notably in crudes, as well as the solid fraction that precipitates when the temperature of the petroleum fluid falls below this critical value. A differentiation is established between n-paraffins, iso-paraffins, naphthenes and aromatics. The model utilizes an analytical representation of the fluids by pseudo-components, the physico-chemical parameters of most of them being determined by combination of the corresponding parameters of a certain number of pure hydrocarbons gathered in a database. The model takes account of the non-ideality of the solid, liquid, and gas phases. Two of the pseudo-constituents including the heaviest fractions are represented by two ficticious molecules, each being defined by a molar distribution among various groups which constitute them, and a group contribution method is used to calculate the thermodynamic properties thereof. The method can be applied for optimization of the production and the transportation of petroleum fluids by means of pipes.

6 Claims, 7 Drawing Sheets

FIG. 2

| PSEUDO-COMPONENTS | WEIGHT PERCENTAGE IN FRACTION $C_{20}^{-}$ | WEIGHT PERCENTAGE IN CRUDE |
|---|---|---|
| P1 | 18% | 8% |
| P2 | 33% | 15% |
| P3 | 22% | 10% |
| P4 | 11% | 5% |
| P5 | 16% | 7% |
| TOTAL | 100% | 45% |
| PSEUDO-COMPONENTS | WEIGHT PERCENTAGE IN FRACTION $C_{20}^{+}$ | WEIGHT PERCENTAGE IN CRUDE |
| P6 | 27% | 15% |
| P7 | 6% | 3% |
| P8 | 27% | 15% |
| P9 | 40% | 22% |
| TOTAL | 100% | 55% |

| Nature of the Groups | Number of Groups |
|---|---|
| Quaternary carbon : C | 2.09 |
| Ternary carbon: CH | 23.32 |
| Secondary carbon: CH2 | 58.75 |
| Primary carbon : CH3 | 15.84 |
| Total | 100 |

FIG.7

| Nature of the Groups | Number of Groups |
|---|---|
| Condensed aromatic carbon : Ccond. | 10.83 |
| Branched aromatic carbon : Cbran. | 17.92 |
| Secondary aromatic carbon : CaroH | 16.04 |
| Quaternary carbon: C | 1.12 |
| Ternary carbon : CH | 9.85 |
| Secondary carbon : CH2 | 35.29 |
| Primary carbon : CH3 | 8.95 |
| Total | 100 |

METHOD FOR MODELING THE CRYSTALLIZATION OF PARAFFINS IN PETROLEUM FLUIDS

FIELD OF THE INVENTION

The present invention relates to a method for achieving a model of the crystallization of paraffins in a petroleum fluid as a function of the composition thereof.

Most petroleum crudes comprise heavy hydrocarbons that include a waxy solid phase at sufficiently low temperatures. The wax that forms deposits on the walls of wells and of pipelines, which notably leads to a pressure drop increase. This is particularly the case with pipelines immersed in cold water whose temperature is often below the cloud point of the fluid. Under extreme conditions, wax deposits may eventually totally clog production and transportation pipes.

It is well-known to add to the fluids to be conveyed chemical additives or solvents likely to impede waxy deposits, but these processes are expensive.

In order to fight against these phenomena, which may have considerable economic consequences, it is important to control the conditions of formation of deposits so as to better prevent them, and notably to be able to calculate the temperature at which paraffins appear, as well as the evolution of the deposits as a function of the temperature.

The object of the method according to the invention is to form a thermodynamic composition model allowing for a mixture of hydrocarbons of given composition, determination of:

the thermodynamic conditions (temperature T and pressure P) at which the crystallization occurs and notably, for a given pressure, the starting crystallization temperature, i.e. that at which the first solid crystals form on cooling of the mixture, and the amount and the composition of the deposits formed for given T and P conditions.

Development of this thermodynamic composition model, which is intended to describe the behaviour of a paraffinic crude, involves:

1) analytical representation of the crude by pseudo-constituents;
2) determination of the physico-chemical quantities which are involved in the various equations of the model and which are characteristic of each of the pseudo-constituents of the fluid studied;
3) selection of the thermodynamic models representing the non-ideal behaviour of the liquid, gas and solid phases.

It is then possible, if data measured in the laboratory are available, to adjust therewith the binary interaction parameter in the solid phase A. Knowledge of this parameter thereafter allows calculation of solid deposit curves when the composition of the mixture studied varies, in particular by addition of a fluxing agent.

BACKGROUND OF THE INVENTION

There are many publications concerned with the formation of paraffin deposits in hydrocarbon mixtures. The following can be mentioned by way of example:

Narayanan L. et al: "Model for Predicting Wax Deposition from Crude Oils", Paper 55a, 1993, AIChE Spring National Convention, March 28–April 1;

Pedersen K. S.: "Prediction of Cloud Point Temperatures and Amount of Wax Precipitation", Paper SPE 27629, Soc. of Pet. Engrs., Richardson, Tex. (1993);

Won K. W.: "Thermodynamics for Solid Solution-Liquid-Vapor Equilibria: Wax Phase Formation from Heavy Hydrocarbon Mixtures", in Fluid Phase Eq. (1986) 30/625.

Many well-known modeling methods comprise using a specific database from which the thermodynamic properties are calculated.

The methods described in these prior publications all overestimate the order of magnitude of the solid deposits experimentally measured with crudes.

The method according to the invention allows building of a model giving a precise account of the crystallization of paraffins in a petroleum fluid as a function of the composition thereof, wherein the petroleum fluid is analyzed so as to define the respective mass fractions of a certain number of pseudo-constituents in limited number, each comprising certain hydrocarbon classes.

SUMMARY OF THE INVENTION

The present invention is characterized in that a database containing the values of determined physico-chemical parameters concerning a certain number N of pure constituent hydrocarbons is made up, and the physico-chemical parameters of each of these pseudo-components are determined by a combination of the corresponding physico-chemical parameters of these hydrocarbons.

The physico-chemical parameters of at least part of the pseudo-components are, for example, determined by linear weighting of the values of a certain number k of corresponding physico-chemical parameters $G_d(i,j)$ of the pure hydrocarbons as a function of the molar compositions $x_i$ in accordance with the relation:

$$G_d(P, j) = \frac{\sum_{i=1}^{\tau} x_i * G_d(i, j)}{\sum_{i=1}^{\tau} x_i}$$

where $\tau$ refers to the number of hydrocarbons represented by pseudo-constituent P;

$x_i$ is the mole percent in the crude of the i-th hydrocarbon ($i=1, \ldots, \tau$) represented by pseudo-constituent P, $G_d(i,j)$ is the j-th parameter among the k parameters of the i-th hydrocarbon;

$G_d(P,j)$ is the j-th parameter among the k parameters of pseudo-constituent P.

The method comprises, for example, description of the petroleum fluid by nine pseudo-constituents.

One chooses to define two pseudo-constituents comprising the heaviest fractions that are represented by two ficticious molecules defined each by a molar distribution among various groups that constitute them, and a group contribution method is used to calculate the thermodynamic properties thereof.

The ficticious molecules are defined, for example, for the pseudo-constituents including all the hydrocarbons in the $C_{20+}$ fraction of the crude, except for the n-alkanes of this fraction.

The method comprises, for example, classing the paraffin deposits formed as a non-ideal single solid phase that can be modeled by a parameter representing the binary interactions in the solid phase.

As specified in the description hereafter, the choices made in the method according to the invention lead to the calculation of the amounts of solid paraffinic deposits in perfect accordance with those measured experimentally.

BRIEF DESCRIPTION OF THE DRAWINGS

Other features and advantages of the method according to the invention will be clear from reading the description hereafter of a non limitative embodiment example, with reference to the accompanying drawings wherein.

DESCRIPTION OF THE INVENTION

Modeling of the crystallization of paraffins according to the invention is achieved in accordance with a system of physical laws well-known to specialists that will be set forth hereafter.

A thermodynamic model has to be selected for the representation of each phase in order to calculate the gas, liquid, solid equilibria. With a set temperature and pressure, the molar ratio between the various solid (S), liquid (L) and gas (G) phases is sought for a crude of given composition.

The liquid (L)/gas (G) and solid (S)/liquid (L) equilibrium conditions of a system consisting of n constituents at equilibrium, which are at the root of the solid deposit calculations of paraffinic crudes, are sought.

At thermodynamic equilibrium, the fugacity fi of component i must be equal in the three phases:

$$f_i^S = f_i^L = f_i^G.$$

The fugacities of the liquid and of the gas of component i are expressed as follows:

$$f_i^L(T,P,x_i^L) = P * x_i^L * \phi_i^L(T,P,x_i^L) \quad (A3)$$

$$f_i^G(T,P,x_i^G) = P * x_i^G * \phi_i^G(T,P,x_i^G) \quad (A4)$$

where $x_i^L$, $x_i^G$, $x_i^S$ represent respectively the molar fractions of "i" in the liquid, gas and solid phases.

The fugacity coefficients in the gas and in the liquid phase are calculated by means of Abdoul and Péneloux's group contribution method described for example by:

Abdoul W., Rauzy E., Péneloux A. (1991): "Group-Contribution Equation of State for Correlating and Predicting Thermodynamic Properties of Weakly Polar and Non-Associating Mixtures. Binary and Multi-Component Systems", Fluid Phase Equilibria, 69, pp. 47–102.

Fugacities in the solid phase are expressed as a function of the activity coefficients $\gamma_i^S$:

$$f_i^S(T,P,x_i^S) = x_i^S * f_i^S(T,P_{ref}) * \gamma_i^S(T,P_{ref},x_i^S) * \exp\int_{P_{ref}}^{P} \frac{\overline{v_i^S}}{RT} * dP. \quad (A5)$$

$P_{ref}$ is a reference pressure. $\overline{v_i}$ is the partial molar volume defined as follows (with V being the volume of the system considered, and $n_i$ being the number of moles of constituent "i"):

$$\overline{v_i} = \left(\frac{\partial V}{\partial n_i}\right)_{T,p,n_{j\neq i}}. \quad (A6)$$

The expression of the liquid/gas $K_i^{LG}$ and the solid/liquid $K_i^{SL}$ partition constants is deduced therefrom:

$$K_i^{LG} = \frac{x_i^L}{x_i^G} = \frac{\phi_i^G}{\phi_i^L(T,P,x_i^L)} \quad (A7)$$

$$K_i^{SL} = \frac{x_i^S}{x_i^L} = \frac{P * \phi_i^L(T,P,x_i^L)}{f_i^S(T,P_{ref})} * \frac{\exp\int_{P_{ref}}^{P} \frac{-\overline{v_i^S}}{RT} * dP}{\gamma_i^S(T,P_{ref},x_i^S)}. \quad (A8)$$

If one considers that there is a solid phase $S_1$—solid phase $S_2$ transition, equation A8 is expressed in the well-known form as follows:

$$\ln\frac{f_i^{L_s}(T,P_{ref})}{f_i^S(T,P_{ref})} = \quad (A9)$$

$$\frac{\Delta g_i^{S \rightarrow L_s}}{RT} = \frac{\Delta h_i^{melting}}{RT} * \left(1 - \frac{T}{T_i^{melting}}\right) + \frac{\Delta h_i^{S-S}}{RT} * \left(1 - \frac{T}{T_i^{S-S}}\right) +$$

$$\frac{C_{Pi}^{L_s} - C_{Pi}^{S_1}}{R} * \left(\ln\frac{T_i^{melting}}{T_i^{S-S}} + \frac{T_i^{S-S} - T_i^{melting}}{T}\right) +$$

$$\frac{C_{Pi}^{L_s} - C_{Pi}^{S_2}}{R} * \left(\ln\frac{T_i^{S-S}}{T} + \frac{T - T_i^{S-S}}{T}\right)$$

and $$f_i^{L_s}(T,P_{ref}) = P * \phi_i^{L_s}(T,P_{ref}) \quad (A10)$$

where $T_i^{melting}$, $T_i^{S-S}$, $\Delta h_i^{S-S}$ are the melting and solid-solid transition temperatures and enthalpies. $C_P L^s$, $C_P S^1$, $C_P S^2$ are the heat-capacity rates of a constituent "i" respectively in the "supercooled" liquid phase and in the solid phase in the crystalline forms $S_1$ or $S_2$ thereof.

The following expression is thus obtained for the solid/liquid partition constant $K_i^{SL}$:

$$K_i^{SL} = \frac{x_i^S}{x_i^{L_s}} = \frac{\phi_i^L(T,P,x_i^L)}{\phi_i^{L_s}(T,P_{ref})} * \frac{\exp\int_{P_{ref}}^{P} \frac{-\overline{v_i^S}}{RT} * dP}{\gamma_i^S(T,P_{ref},x_i^S)} * \exp\left(\frac{\Delta g_i^{S \rightarrow L_s}}{RT}\right). \quad (A11)$$

Pseudo-Constituents

The model achieved according to the invention being of the molecular composition type, it requires knowledge of the molar composition of the crude, and therefore of a considerable amount of data, since up to about 500 different hydrocarbons can be identified in a crude. It turns out that it is impossible in practice to consider all of these data since:

1) the physico-chemical quantities (Tc, Pc, ω, melting temperatures and enthalpy, etc) concerning notably the non "n-paraffinic" compounds are not known once their number of carbon atoms is above 10, and 2) the calculating time required would be too long for the industrial applications of the model achieved.

Thus, all of the hydrocarbons, both the constituents perfectly identified by gas chromatography and those whose number of carbon atoms and chemical family alone are known, have been collected into a certain number of groups or pseudo-constituents.

It has been decided to represent the fluids preferably by nine pseudo-constituents, five for the $C_{20-}$ fraction and four for the $C_{20+}$ fraction.

In order to determine the starting crystallization temperature and the amount of deposition of the crude, it is necessary to know a certain number k of physico-chemical quantities or parameters proper to each of the pseudo-constituents representative of the fluid studied, nine in number for example:

1. molar mass, MM;
2. melting temperature, $T_{melting}$;
3. solid-solid transition temperature, $T_{SS}$;
4. melting enthalpy, $\Delta h_{melting}$;
5. solid-solid transitions enthalpy, $\Delta h_{SS}$;
6. critical temperature, $T_C$;
7. critical pressure, $P_C$;
8. acentric factor, ω;
9. molecular conformation parameter $l_i$.

The method according to the invention includes making up a database in which the physico-chemical quantities or parameters defined above, relative to a number N of pure hydrocarbons (N=75 for example), are gathered together. It is from these pure hydrocarbons that the corresponding physico-chemical parameters that are assigned to at least part of the pseudo-constituents are calculated.

For each of the pseudo-constituents of the $C_{20-}$ fraction, the k quantities $G_d(P,j)$ are calculated according to the relation as follows:

$$G_d(P, j) = \frac{\sum_{i=1}^{\tau} x_i * G_d(i, j)}{\sum_{i=1}^{\tau} x_i}, \text{ where} \quad (3)$$

τ is the number of hydrocarbons represented by pseudo-constituent P;

$x_i$ is the mole percent in the crude of the i-th hydrocarbon (i=1, . . . , τ) represented by pseudo-constituent P;

$G_d(i,j)$ is the j-th property among the above-mentioned nine of the i-th hydrocarbon;

$G_d(P,j)$ is the j-th property among the above-mentioned nine of pseudo-constituent P.

When the molar masses of each of the pseudo-constituents has been calculated, their mole percentages in the crude is obtained from the mass percentages.

Fractionation of a Crude to be Modeled

Figure 1:
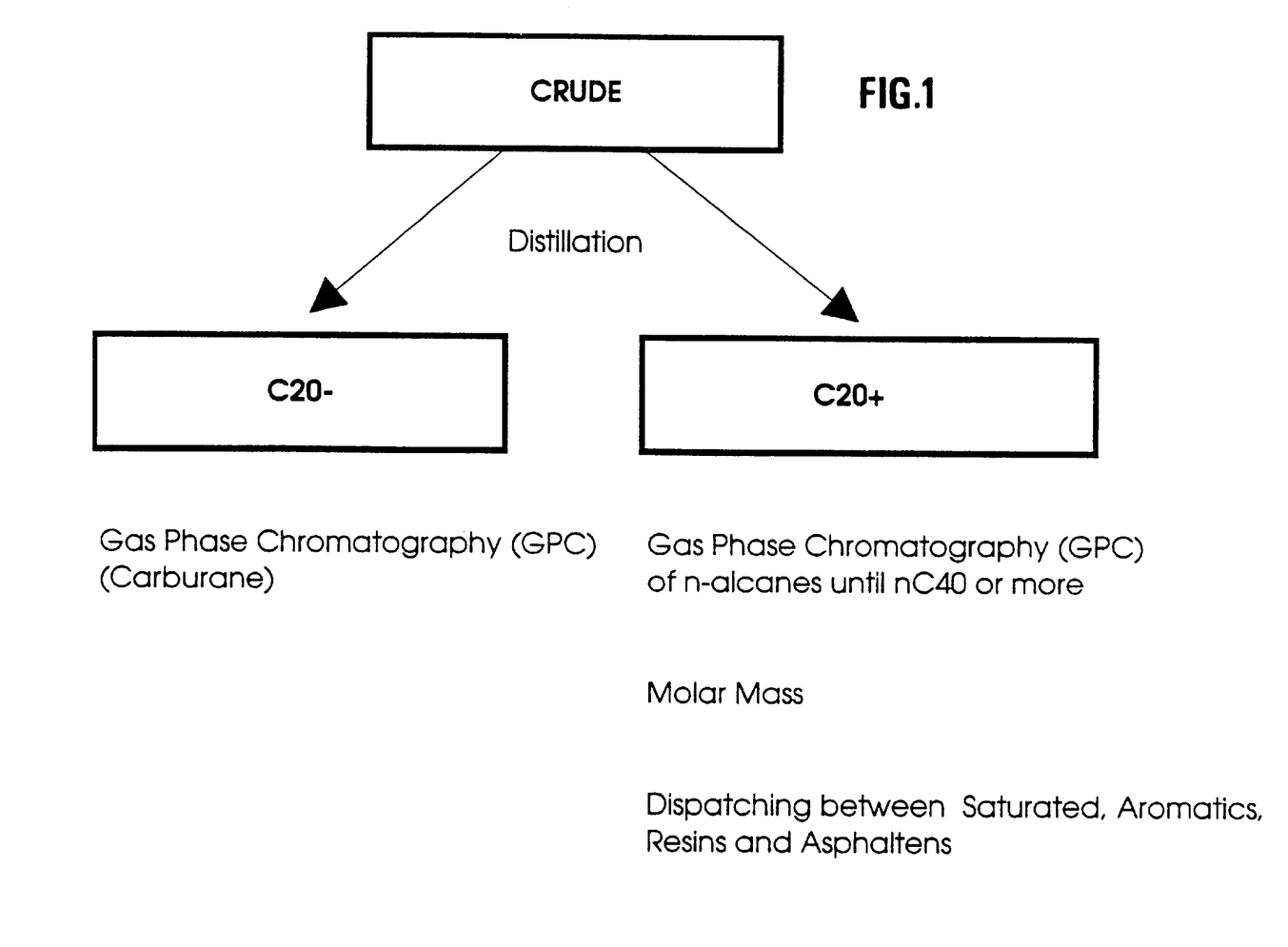
FIG. 1 is a diagram of the analytical operations to be performed on a crude.

As shown in FIG. 1, a crude to be modeled is first fractionated by means of a $C_{20}$ distillation process allowing separation of the two $C_{20-}$ and $C_{20+}$ fractions and knowing the mass ratio thereof. Each of the fractions thus obtained is analyzed differently.

Analysis of the $C_{20-}$ Fraction

The $C_{20-}$ fraction is analyzed by gas chromatography (GC), preferably according to the method known as "Carburane", described by:

DURAND J. P. et al: "Direct and Automatic Capillary GC Analysis for Molecular Weight Determination and Distribution in Crude Oils and Condensates up to $C_{20}$", J. of High Resolution Chromatography, 12, 1989, p.230.

This type of analysis is an integral part of the petroleum fluid analysis protocol developed within the framework of ARTEP, and it has led to the complete identification of all the hydrocarbons up to $nC_{11}$, of all the n-alkanes up to $nC_{20}$, to the distribution among the iso-alkanes, naphthenes and aromatics per fraction of a carbon atom between $nC_{11}$ and $nC_{15}$, and to a distribution among the saturated hydrocarbons and aromatics per fraction of a carbon atom between $nC_{15}$ and $nC_{20}$.

This $C_{20-}$ fraction is represented by five pseudo-constituents P1, P2, P3, P4 and P5:

P1 and P2 represent the n-alkanes whose number of carbon atoms is less than or equal to 20;

P3 is the pseudo-constituent representative of the iso-alkanes of the $C_{20-}$ fraction;

P4 is the pseudo-constituent representative of the naphthenes of the $C_{20-}$ fraction;

P5 is the pseudo-constituent representative of the aromatics of the $C_{20-}$ fraction.

Analysis of the $C_{20+}$ Fraction

The analytical quantities to be acquired for the $C_{20+}$ fraction are: the distribution of the n-alkanes up to $nC_{40}$ or more, the molar mass of the fraction, and the distribution among saturated hydrocarbons, aromatics, resins and asphaltenes. The influence of asphaltenes on paraffinic deposits is considered to be negligible.

In order to develop the thermodynamic model, it has been decided to measure:

1) the distribution of the n-paraffins by gas chromatography (GC) up to $nC_{40}$;

2) the molar mass of the $C_{20+}$ fraction by tonometry;

3) the distribution among saturated hydrocarbons, aromatics and resins by liquid chromatography of the $C_{20+}$ fraction. The SAR, i.e. the distribution in percent by weight among each of these chemical families, is then obtained for this fraction.

This $C_{20+}$ fraction is represented by four pseudo-constituents P6, P7, P8 and P9:

P6 and P7 represent the n-alkanes whose number of carbon atoms is above 20;

P8 is the pseudo-constituent representative of the non n-paraffinic saturated hydrocarbons (all of the iso-alkanes and the naphthenes) of the $C_{20+}$ fraction;

P9 is the pseudo-constituent representative of the non-saturated molecules aromatics, resins, asphaltenes) of the $C_{20+}$ fraction.

The following analytical data are available for the pseudo-constituents P8 and P9:

mass distribution among the various chemical families: saturated hydrocarbons and aromatics+resins;

structural units by NMR of the $^{13}C$ of each of these families.

Figure 6:
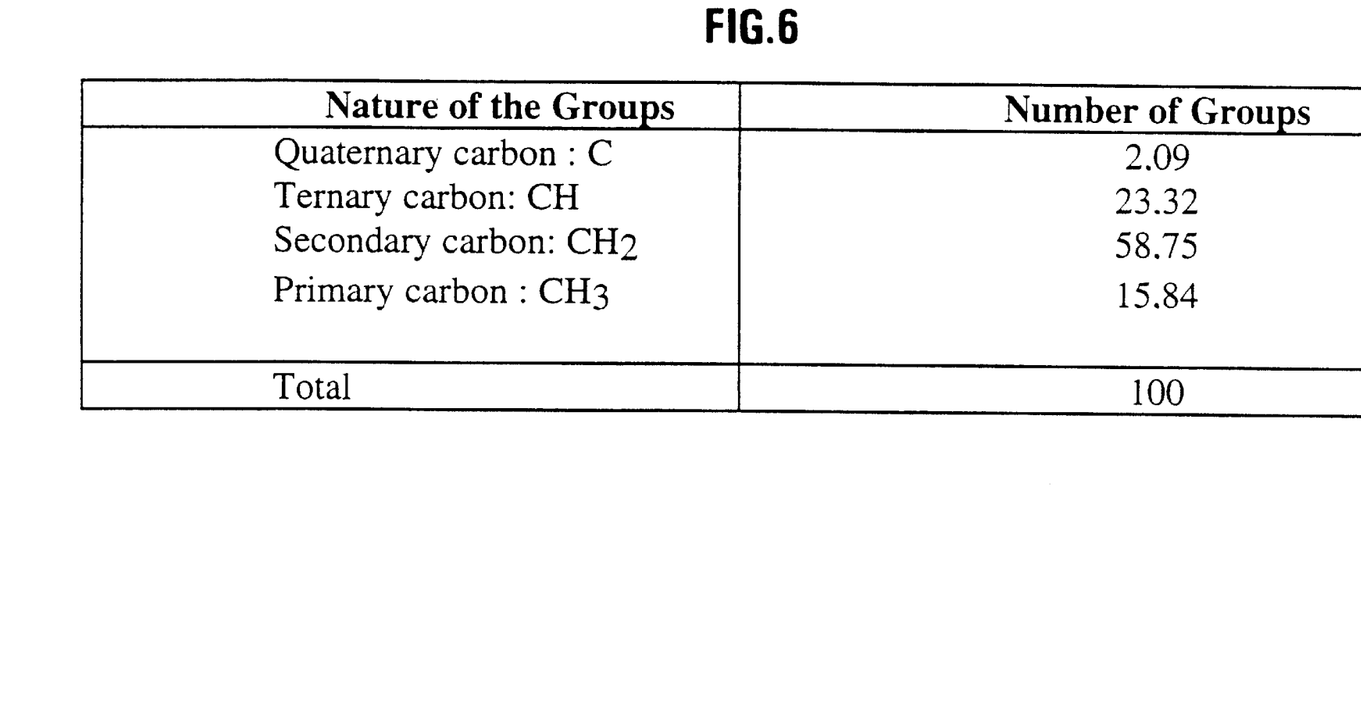
FIG. 6 is a table showing the nature and the number of groups constituting the ficticious molecule of the pseudo-constituent P8.
Figure 7:
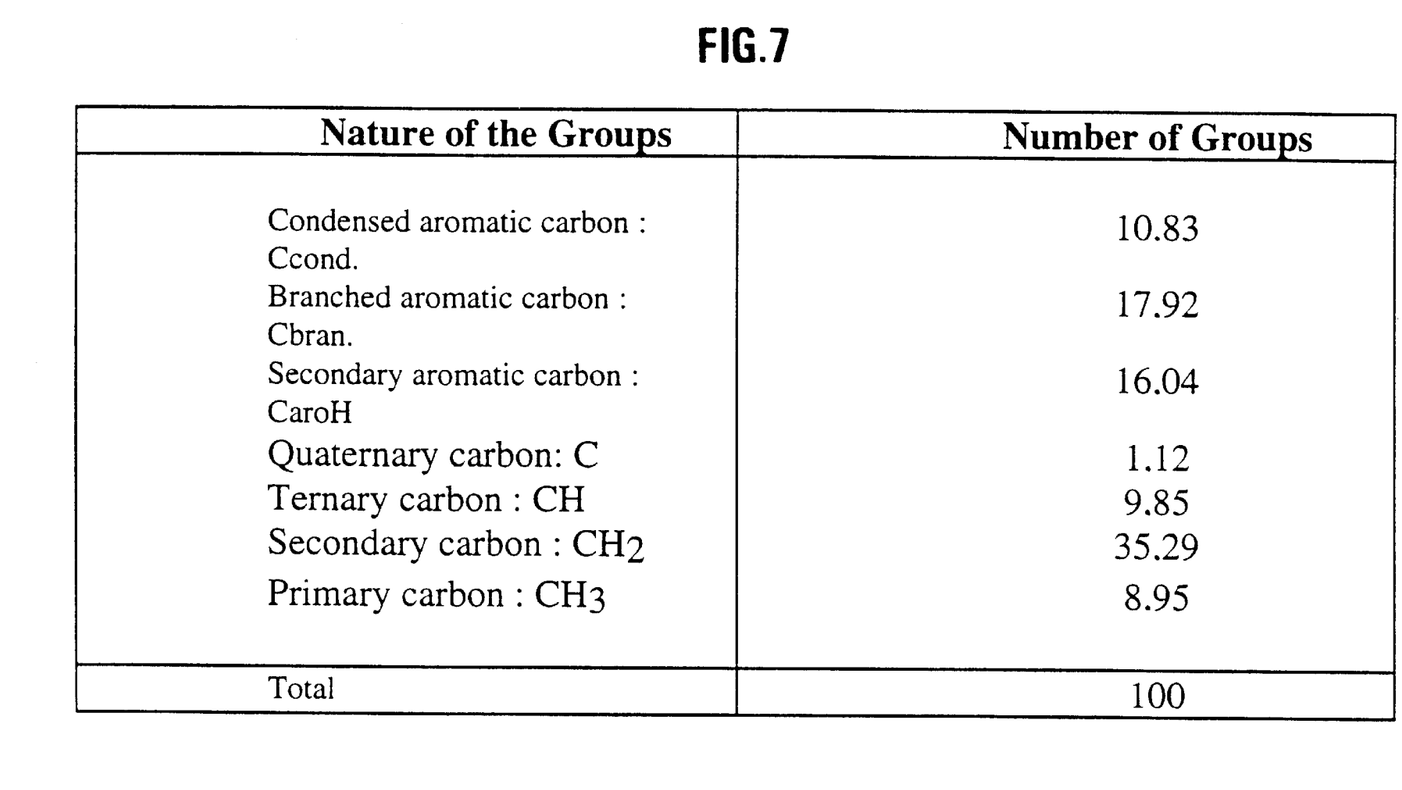
FIG. 7 is a table showing the nature and the number of groups constituting the ficticious molecule of the pseudo-constituent P9.

The method according to the invention also comprises creating, for each of the pseudo-constituents P8 and P9, a ficticious molecule characterized by the molar distribution thereof among the various groups that constitute it (see FIGS. 6 and 7).

This distribution allows defining the pseudo-constituents P8 and P9 and calculation of the physico-chemical properties thereof (Tc, Pc, ω, etc), provided that the molar mass (respectively $MM_{P8}$ and $MM_{P9}$) and the number of carbon atoms thereof ($C_{P8}$ and $C_{P9}$) are known.

Besides determination of the two ficticious molecules, the analysis results of the crudes collected in the database have also allowed establishing a relation between the molar mass of P8 and that of P9:

$$MM_{P8}=1.33*MM_{P9} \quad (5).$$

Knowing the molar mass of the $C_{20+}$ fraction: $MMC_{20+}$, the percent by weight in the crude of the "non n-paraffinic saturated hydrocarbons" pseudo-constituent P8 and that of the "unsaturated hydrocarbons" pseudo-constituent P9, the molar masses $MM_{P8}$ and $MM_{P9}$ are respectively determined by means of equations (5) and (6):

$$MM_{C20^+} = \frac{p(P6)+p(P7)+p(P8)+p(P9)}{\frac{p(P6)}{MM_{P6}}+\frac{p(P7)}{MM_{P7}}+\frac{p(P8)}{MM_{P8}}+\frac{p(P9)}{MM_{P9}}} \quad (6)$$

where Pi is pseudo-constituent No. i (i=1, . . . , 9);

p(Pi) is the percent by weight in the crude of pseudo-constituent Pi;

$MM_{Pi}$ is the molar mass of pseudo-constituent Pi.

The data relative to the pseudo-constituents representative of the n-alkanes of the $C_{20+}$ fraction being known (P6 and P7), equations (5) and (6) allow the unknowns $MM_{P8}$ and $MM_{P9}$ to be calculated.

The following ratio can be obtained from the empirical formula of the ficticious molecules of P8 and P9:

$$RPi = \frac{\text{number of hydrogen atoms of psuedo-constituent Pi}}{\text{number of carbon atoms of psuedo-constituent Pi}}$$

We thus obtain: RP8=1.88 and RP9=1.2332.

The number of carbon atoms $C_{P8}$ and $C_{P9}$ is determined according to equations (7) and (8):

$$C_{P8} = \frac{MM_{P8}}{MM_C + RP8*MM_H}, \quad (7)$$

and $$C_{P9} = \frac{MM_{P9}}{MM_C + RP9*MM_H} \quad (8)$$

where $MM_C$ is the atomic mass of carbon (close to 12 g), and $MM_H$ is the atomic mass of hydrogen (close to 1 g).

Determination of the Physico-Chemical Quantities of Pseudo-Constituents P8 and P9

For pseudo-constituents P8 and P9, which are not generated from identified hydrocarbons, it is necessary to calculate the nine physico-chemical properties and to enter them into the data file. In order to calculate all the physico-chemical quantities of these pseudo-constituents by means of group contribution methods, it is necessary to calculate first quantity No. 9, i.e. the parameters of Abdoul and Péneloux's model (1987) defined above.

The number N(Pi) of the groups that constitute each of the pseudo-constituents is calculated by means of the following relation from the numbers of groups of ficticious molecules, the respective numbers of carbon atoms $C_{Pi}$ (i=8 or 9) of pseudo-constituents Pi:

N(Pi)=$C_{Pi}$/100*Number of groups of the ficticious molecule of Pi.

Distribution of the Pseudo-Constituents in the Crude

The weight percentage of pseudo-constituents P1 to P5 in the $C_{20-}$ fraction and the weight percentage of pseudo-constituents P6 to P9 in the $C_{20+}$ fraction are calculated. The weight percentage of all of the 9 pseudo-constituents in the crude is calculated by weighting, by means of the results from the crude distillation.

Figure 2:
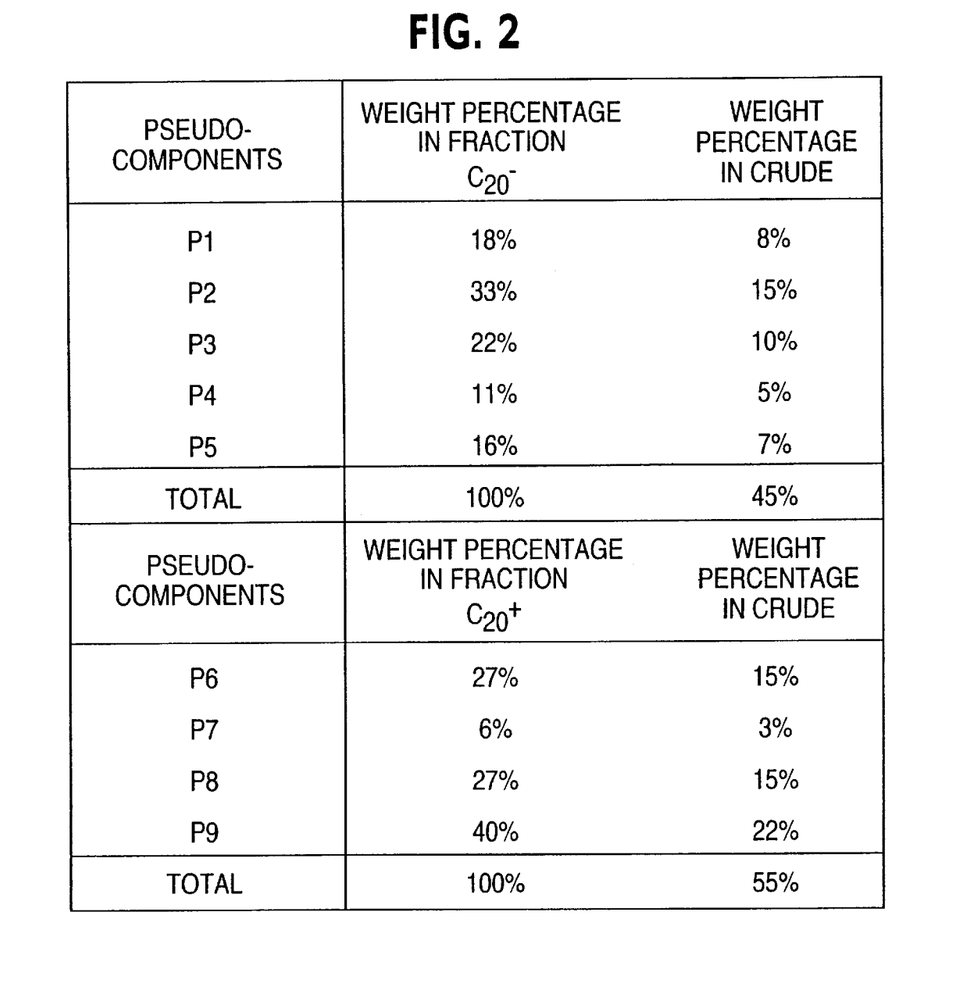
FIG. 2 is a table showing an example of calculation of the mass percentages of pseudo-constituents P1 to P9 in a crude, the mass percentages thereof in the $C_{20-}$ or $C_{20+}$ fractions being known, and the results obtained from the crude distillation.

The table of FIG. 2 shows an example where the weight percentage in the crude of pseudo-constituents P1 to P9 were calculated from the following results:

$P_{C20-}$=45%

$P_{C20+}$=55%

Adjustment of the Binary Interaction Parameter in the Solid Phase

To implement the method according to the invention, it has been decided to class the deposits formed as a non-ideal single solid phase and to express the excess Gibbs energy of this phase by means of an empirical relation whose parameter(s) can be adjusted on the experimental results (in particular the solid deposit curve). The equation in a single parameter proposed by Margules, well-known to specialists, has been selected to that effect. It presents the advantage of having the simplest possible expression among those giving the molar excess Gibbs energy:

$$g^E = \sum_{i=1}^{n}\sum_{j=i+1}^{n} A_{ij}(T)*x_i^S*x_j^S \quad (A12)$$

where $A_{ij}$ is the binary interaction parameter in the solid phase between constituents i and j. Knowledge of the function $g^E$ allows calculation of the activity coefficients in the solid phase:

$$RT\ln\gamma_i^S = \left(\frac{\partial ng^E}{\partial n_i}\right)_{T,P,n_j} = -g^E + \sum_{j=1,j\neq i}^{n} A_{ij}(T)*x_j^S. \quad (A13)$$

It has been considered that the binary interaction parameters in the solid phase are all identical and equal to parameter A, i.e.:

$$\begin{cases} A_{ij} = A_{ji} = A \text{ with } i \neq j \\ \text{and} \\ A_{ii} = 0 \end{cases} \quad (A14)$$

The following expression results therefrom for the solid/liquid partition constants:

$$K_i^{SL} = \frac{x_i^S}{x_i^L} = \frac{\varphi_i^L(T, P, x_i^L)}{\varphi_i^{L_s}(T, P_{ref})} * \frac{\exp(\Delta g_i^{S \to L_s} / RT)}{\gamma_i^S(T, P_{ref}, x_i^S)} \quad \text{(A15)}$$

where:

$$\frac{\Delta g_i^{S \to L_s}}{RT} = \frac{\Delta h_i^{melting}}{RT} * \left(1 - \frac{T}{T_i^{melting}}\right) + \frac{\Delta h_i^{S-S}}{RT} * \left(1 - \frac{T}{T_i^{S-S}}\right) \quad \text{(A16)}$$

and where the $\gamma_i^S$ are given by equations (A12) to (A14).

The partition constants $K_i^{LG}$ (equation A7) and $K_i^{SL}$ (equation A15) allow access to the molar compositions $x_i$ of each of the constituents in each of the phases at equilibrium, and therefore to the ratio sought (i.e. the ratio in number of moles of the amount of solid deposits S to the total number of moles of the crude F).

Figure 3:
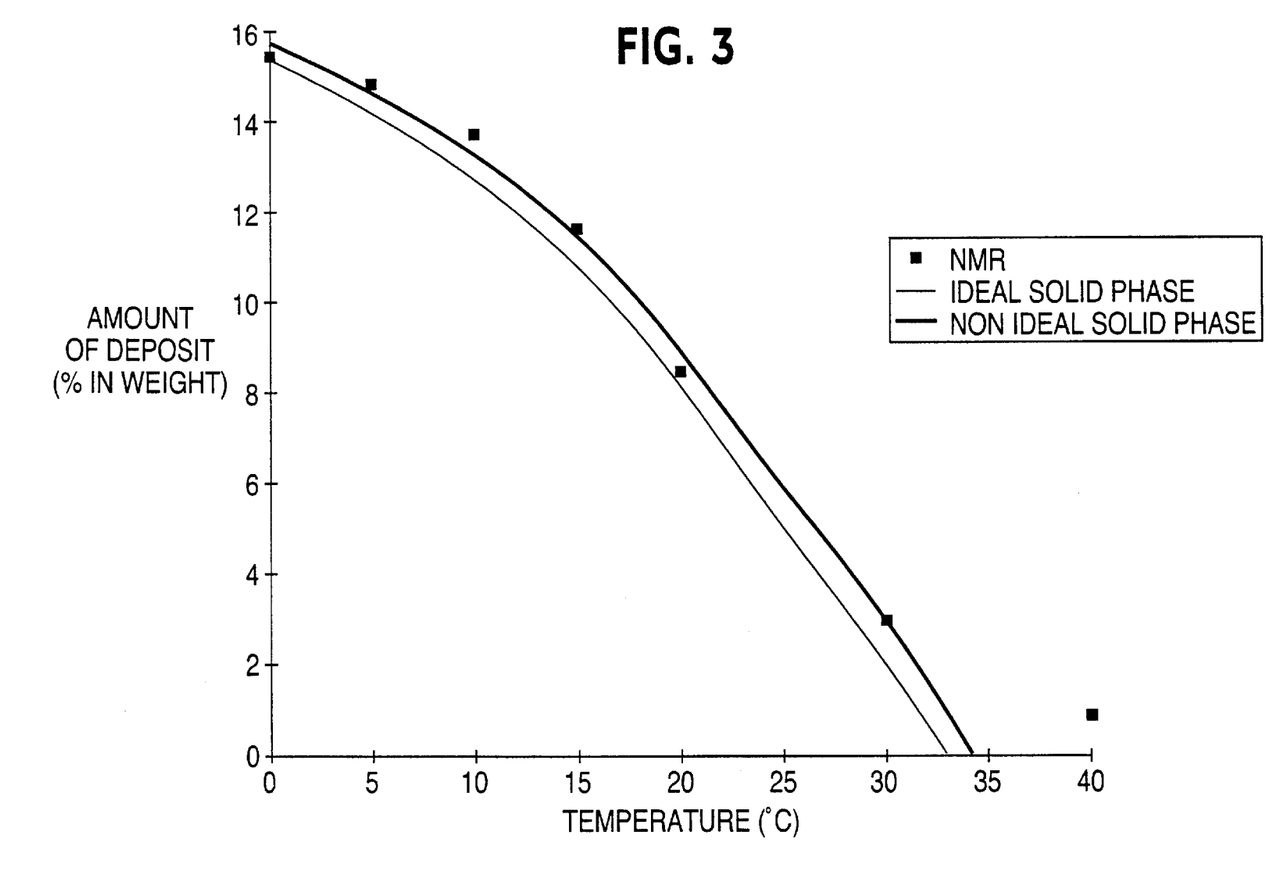
FIG. 3 shows a comparison of the calculated solid deposit curves and of those obtained experimentally by means of a NMR technique.
Figure 4:
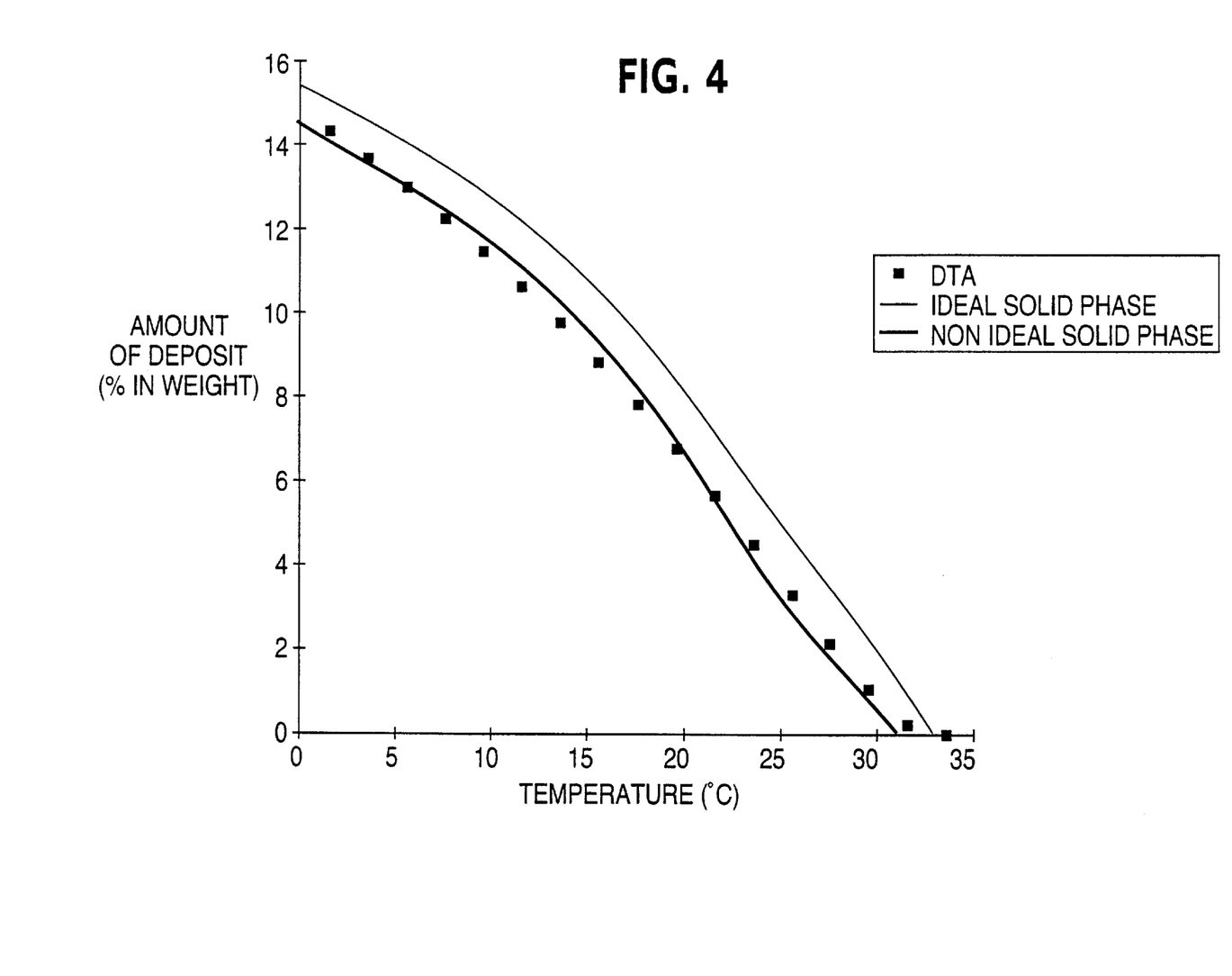
FIG. 4 shows a comparison of the calculated solid deposit curves and of those obtained experimentally by means of a technique referred to as DTA.
Figure 5:
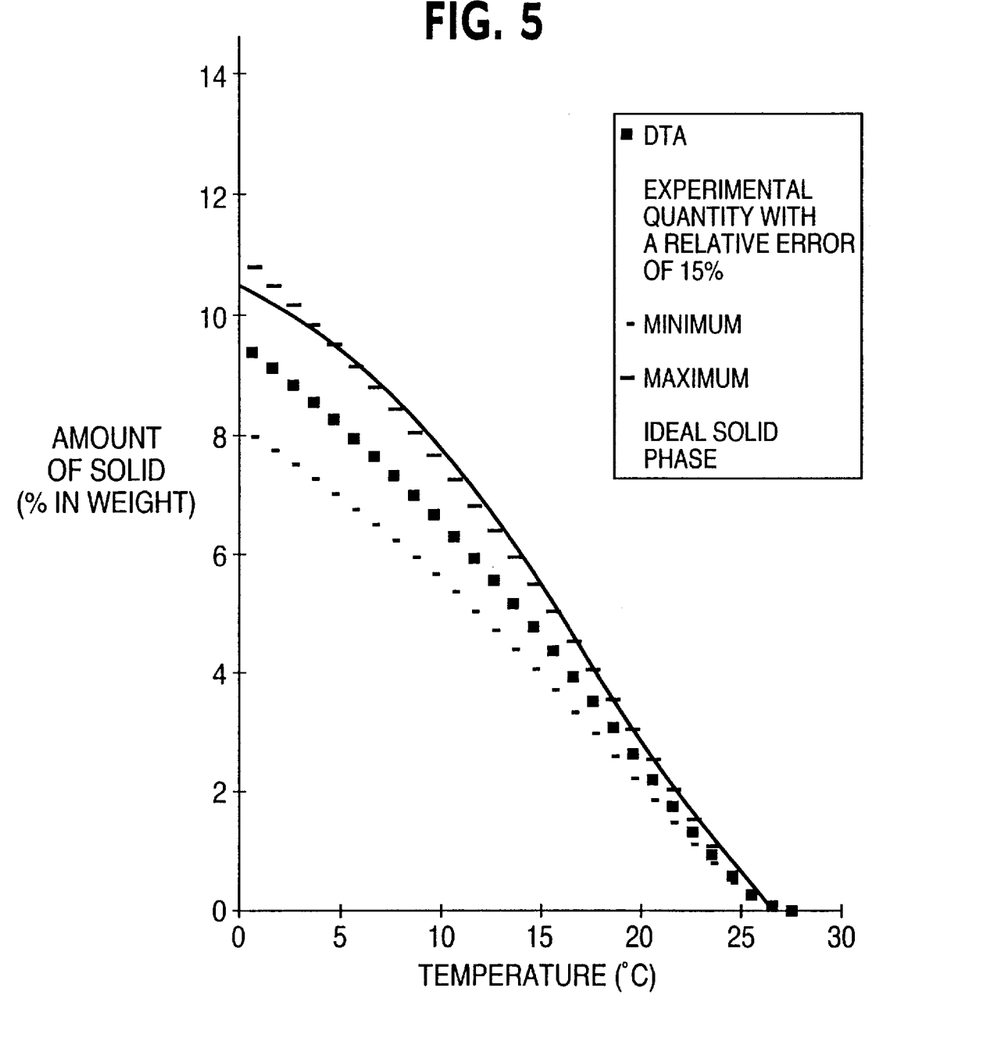
FIG. 5 shows a comparison of the calculated solid deposit curves and of those obtained experimentally by means of the DTA technique in the case of a crude fluxed by adding a light condensate.

The modeling equation in a single parameter A used only requires adjustment of a single parameter A which represents the binary interactions in the solid phase. It has been checked that the results calculated with this equation in order to represent the solid phase are in accordance with the experimental results (FIGS. 3, 4). This parameter is identical for all the binaries involved in the solid mixture. Knowledge of parameter A allows calculation of the solid deposit curves of the fluids whose composition has slightly varied (through addition of a fluxing agent for example, as shown in FIG. 5).

Adjustment of A is achieved from the solid deposit curve measured in the laboratory with the original crude. It is performed by means of a least-squares method on all of the points of the curve.

Experimental Validation

The analytical representation in nine pseudo-constituents of the method according to the invention has been applied to a crude and, for each of them, the physico-chemical quantities (characteristic triplet, melting temperature and enthalpy, etc.) have been determined.

The calculated results have been compared with those resulting from two experimental techniques: the NMR and the DTA (Differential Thermal Analysis) techniques, and the comparative results are shown in FIGS. 3 and 4.

A good display of the starting crystallization temperature (Tcc) is obtained when the calculations are carried out with an ideal solid phase (i.e. in predictive mode). The results calculated on the solid deposit amounts are very close to the experimental results. The calculated amounts are between the results obtained by means of the two experimental techniques.

A light condensate of five n-alkanes between $nC_5$ and $nC_9$ was prepared. The following was prepared thereafter:

80% by weight of crude+20% by weight of light condensate.

The solid deposit curve of the crude thus fluxed was then measured by DTA, and the measurements were compared with the calculated results when:
1) a=0, i.e. in predictive mode (ideal solid phase),
2) a=parameter of the non ideal solid phase, determined previously, when the latter was adjusted on the experimental results obtained by DTA on the crude analyzed.

All these curves are shown in FIG. 5.

In view of a relative experimental error of the order of 15%, it is checked that the results calculated on the deposit amounts with a non ideal solid phase are contained in the range of uncertainty of the experimental measurements.

We claim:

1. A method of modeling thermodynamic conditions causing crystallization of paraffins in a petroleum fluid as a function of the composition thereof, said method comprising the steps of:

(a) analyzing the petroleum fluid to define respective mass fraction of a certain number of pseudo-constituents in limited number including each determined hydrocarbon class;

(b) storing values of determined physico-chemical parameters concerning a certain number of pure constituent hydrocarbons in a database; and (c) determining physico-chemical parameters of at least part of said pseudo-constituents by combination of the corresponding physico-chemical parameters of said pseudo-constituents.

2. A method as claimed in claim 1, wherein step (c) comprises linear weighting of values of a certain number of corresponding physico-chemical parameters $G_d(i,j)$ of some pure hydrocarbons as a function of a molar compositions $x_i$, in accordance with the relation:

$$G_d(P, j) = \frac{\sum_{i=1}^{\tau} x_i * G_d(i, j)}{\sum_{i=1}^{\tau} x_i}$$

where:

$\tau$ is a number of hydrocarbons represented by pseudo-constituent P;

$x_i$ is a mole percent in the fluid of the i-the hydrocarbon (i=1, . . . , $\tau$) represented by pseudo-constituent P;

$G_d(i,j)$ is a j-th parameter among the k parameters of the i-th hydrocarbon, and $G_d(P,j)$ is j-th parameter among the k parameters of pseudo-constituent P.

3. A method as claimed in claim 1, further comprising describing the petroleum fluid by nine pseudo-constituents.

4. A method as claimed in claim 3, further comprising defining two pseudo-constituents including the heaviest fractions of hydrocarbons, said two pseudo-constituents being represented by two fictitious molecules, each defined by a molar distribution among various groups that constitute them, and using a group contribution method to calculate the thermodynamic properties thereof.

5. A method as claimed in claim 4, comprising defining fictitious molecules for pseudo-constituents including all the hydrocarbons in the $C_{20+}$ fraction of the petroleum fluid, except for the n-alkanes of this fraction.

6. A method as claimed in claim 1, further comprising classifying paraffin deposits formed as a non ideal single solid phase that can be modeled by means of a parameter representing binary interactions in the solid phase.

* * * * *